US009618455B2

(12) United States Patent
Cohen (10) Patent No.: US 9,618,455 B2
(45) Date of Patent: Apr. 11, 2017

(54) CLAM-SHELL LUMINOMETER (71) Applicant: Beri Cohen, Hartsdale, NY (US)

(72) Inventor: Beri Cohen, Hartsdale, NY (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 12 days.

(21) Appl. No.: 14/422,886

(22) PCT Filed: Aug. 6, 2013

(86) PCT No.: PCT/US2013/053714
§ 371 (c)(1),
(2) Date: Feb. 20, 2015

(87) PCT Pub. No.: WO2014/031327
PCT Pub. Date: Feb. 27, 2014

(65) Prior Publication Data
US 2015/0247806 A1 Sep. 3, 2015

Related U.S. Application Data (60) Provisional application No. 61/684,830, filed on Aug. 20, 2012.

(51) Int. Cl.
G01N 21/76 (2006.01)
G01N 33/53 (2006.01)
G01N 21/25 (2006.01)

(52) U.S. Cl.
CPC .......... G01N 21/76 (2013.01); G01N 21/253 (2013.01); G01N 33/5302 (2013.01);
(Continued)

(58) Field of Classification Search
CPC ................ G01N 21/76; G01N 33/53
(Continued)

(56) References Cited

U.S. PATENT DOCUMENTS 1,938,004 A * 12/1933 Baden .................. G01N 21/251
250/373
4,099,920 A * 7/1978 Heiss .................... B01F 9/0014
356/244

(Continued)

FOREIGN PATENT DOCUMENTS

EP 0580362 A1 1/1994
EP 0718622 B1 6/1996
EP 0984270 B1 9/2003

OTHER PUBLICATIONS

PCT International Search Report and Written Opinion dated Mar. 31, 2014 (17 Pages).

(Continued)

Primary Examiner — Arlen Soderquist (57) ABSTRACT

A clam-shell luminometer that, when closed, completely encloses an assay reaction mixture-containing reaction vessel and some portion of a reaction carousel or ring. The luminometer includes first and second portions that are coupled to each other, a photomultiplier tube, and plural fiber optic bundles that are optically coupled to the photomultiplier tube. First ends of the fiber optic bundles are disposed adjacent to the reaction vessel in the second portion so that the fiber optic bundles completely surround the perimeter or periphery of the reaction vessel.

32 Claims, 5 Drawing Sheets (52) U.S. Cl.
CPC ............ *G01N 2201/0221* (2013.01); *G01N 2201/064* (2013.01); *G01N 2201/08* (2013.01); *G01N 2201/084* (2013.01); *G01N 2201/0833* (2013.01)

(58) Field of Classification Search
USPC ..... 422/53, 63–67, 82.05, 82.09; 436/43–55, 436/172
See application file for complete search history.

(56) References Cited

U.S. PATENT DOCUMENTS

| | | | | |
|---|---|---|---|---|
| 4,213,764 | A * | 7/1980 | O'Connor | G01N 33/54346 250/574 |
| 4,250,394 | A * | 2/1981 | O'Connor | G01N 33/54313 250/574 |
| 4,291,230 | A * | 9/1981 | Heiss | G01N 21/645 250/458.1 |
| 4,319,842 | A * | 3/1982 | Priarone | G01N 21/645 250/458.1 |
| 4,349,510 | A * | 9/1982 | Kolehmainen | G01N 21/76 250/328 |
| 4,472,352 | A * | 9/1984 | Quesneau | G01N 21/76 422/52 |
| 4,586,818 | A * | 5/1986 | Lohr | G01N 21/76 356/244 |
| 4,657,390 | A * | 4/1987 | Doyle | G01J 3/453 356/244 |
| 4,685,801 | A * | 8/1987 | Minekane | G01N 21/253 356/328 |
| 4,713,974 | A * | 12/1987 | Stone | G01N 30/24 422/64 |
| 4,730,933 | A * | 3/1988 | Lohr | G01N 21/76 356/244 |
| 4,826,660 | A * | 5/1989 | Smith | G01N 21/255 356/246 |
| 4,863,690 | A * | 9/1989 | Berthold | G01N 21/13 422/510 |
| 4,985,631 | A * | 1/1991 | Wannlund | B01L 3/5025 250/361 C |
| 5,082,628 | A * | 1/1992 | Andreotti | G01N 21/76 250/361 C |
| 5,089,424 | A * | 2/1992 | Khalil | G01N 33/521 422/562 |
| 5,139,745 | A * | 8/1992 | Barr | G01N 21/76 250/361 C |
| 5,401,465 | A * | 3/1995 | Smethers | G01N 21/76 356/440 |
| 5,422,075 | A * | 6/1995 | Saito | G01N 21/76 250/361 C |
| 5,447,687 | A * | 9/1995 | Lewis | G01N 21/76 250/361 C |
| 5,449,621 | A * | 9/1995 | Klein | G01N 15/042 356/426 |
| 5,456,883 | A * | 10/1995 | Burkovich | G01N 35/025 422/547 |
| 5,516,409 | A * | 5/1996 | Kambara | G01N 27/44721 204/603 |
| 5,607,643 | A * | 3/1997 | Xiaoming | G01N 21/65 356/244 |
| 5,637,874 | A | 6/1997 | Honzawa et al. | |
| 5,656,807 | A * | 8/1997 | Packard | H01J 43/246 250/214 VT |
| 5,686,046 | A * | 11/1997 | Malek | G01N 21/13 250/361 C |
| 5,714,388 | A | 2/1998 | Kusnetz | |
| 5,798,263 | A * | 8/1998 | Wood | G01N 21/763 250/361 C |
| 5,919,647 | A * | 7/1999 | Hiramatsu | G01N 21/64 435/287.1 |
| 6,071,748 | A * | 6/2000 | Modlin | B01L 9/523 250/459.1 |
| 6,123,903 | A * | 9/2000 | Tajima | G01N 21/75 250/361 C |
| 6,191,852 | B1 * | 2/2001 | Paffhausen | G01N 21/6452 356/244 |
| 6,290,912 | B1 | 9/2001 | Doms | |
| 6,369,893 | B1 * | 4/2002 | Christel | B01J 19/0093 250/458.1 |
| 6,653,150 | B1 * | 11/2003 | Reed | G01N 15/0211 436/164 |
| 6,660,469 | B1 * | 12/2003 | Wright | G01N 33/04 220/203.08 |
| 6,922,241 | B2 * | 7/2005 | Kramer | G01N 15/1459 356/338 |
| 7,879,290 | B2 * | 2/2011 | Noda | C12Q 1/04 422/52 |
| 7,951,329 | B2 * | 5/2011 | Malyarov | G01N 21/645 356/244 |
| 2003/0194349 | A1 | 10/2003 | Carey et al. | |
| 2004/0067164 | A1 | 4/2004 | Vanbrunt et al. | |
| 2006/0133959 | A1 | 6/2006 | Wang et al. | |
| 2008/0261294 | A1 * | 10/2008 | Noda | G01N 21/76 435/286.2 |
| 2009/0053751 | A1 | 2/2009 | Magrisso et al. | |
| 2010/0054991 | A1 | 3/2010 | Freeman et al. | |
| 2010/0208256 | A1 | 8/2010 | Tang | G01N 21/0303 356/326 |
| 2011/0057117 | A1 * | 3/2011 | Fawcett | B01L 7/52 250/458.1 |

OTHER PUBLICATIONS

Extended EP Search Report dated Nov. 23, 2016 of corresponding European Patent Application No. 13830276.5, 5 Pages.

* cited by examiner

CLAM-SHELL LUMINOMETER

CROSS REFERENCE TO RELATED APPLICATIONS

This patent application claims priority from PCT Patent Application No. PCT/US2013/053714, filed Aug. 6, 2013, which claims the benefit of U.S. Provisional Patent Application No. 61/684,830, filed Aug. 20, 2012, the disclosures of which are incorporated by reference herein in their entirety.

STATEMENT REGARDING FEDERALLY SPONSORED RESEARCH OR DEVELOPMENT

Not Applicable

BACKGROUND OF THE INVENTION

As is well known to those of ordinary skill in the art, state-of-the-art, fully-automated immunoassay analyzers measure chemical constituents of interest within a multiplicity of assays, e.g., body fluids, blood, serum, plasma, urine, and the like. The analyzers process a multiplicity of immunoassays that require separation of chemical constituents of interest, which, typically, are bound to component-selective particles, from free or unbound components in the assay. Automation of the immunoassay process lowers cost, primarily by increasing the throughput of assay reaction mixtures and by reducing the number of personnel required to perform analyses and steps that, heretofore, were performed manually.

However, as advantageous as that may be for some users, the state-of-the-art of fully-automated immunoassay analyzers has reached a level that makes the devices prohibitively expensive especially for emerging markets that cannot afford top-of-the-line analyzers. Therefore, to make analyzers more affordable, it would be desirable to reduce the cost by reducing the level of automation and by incorporating fewer and simpler mechanisms.

BRIEF SUMMARY OF THE INVENTION

A low-cost immunoassay analyzer for emerging markets is disclosed. In pertinent part, the lower-cost immunoassay analyzer includes a luminometer having first and second portions that are coupled to each other to operate in like manner to a clam-shell, a light intensity-measuring device, and plural fiber optic bundles that are optically coupled to the photomultiplier tube of the luminometer. When the clam-shell luminometer is in a closed position, the luminometer completely encloses an assay reaction mixture-containing reaction cuvette above and below the carousel or reaction ring.

The upper portion of the clam-shell luminometer includes a light-generating reagent conduit for dispensing a desired volume of a light-generating reagent into the reaction cuvette enclosed by the clam-shell. The lower portion of the clam-shell luminometer includes a plurality of fiber optic bundles. The first, exposed ends of the fiber optic bundles are collectively disposed adjacent to the reaction cuvette so as to completely surround the perimeter or periphery and the bottom of the reaction cuvette, to collect light emitted during the reaction between the added light-generating reagent and the assay reaction mixture. The second ends of the fiber optic bundles are optically connected to one or more light-intensity-measuring device, e.g., a photomultiplier tube, which processes intensity and wavelength data to provide information about the chemical constituents of the assay reaction mixture.

BRIEF DESCRIPTION OF THE SEVERAL VIEWS OF THE DRAWINGS

Other features and advantages of the invention will be apparent from the following description of embodiments thereof and from the claims, taken in conjunction with the accompanying drawings, in which:

DETAILED DESCRIPTION OF THE INVENTION

Figures 1, 2A:
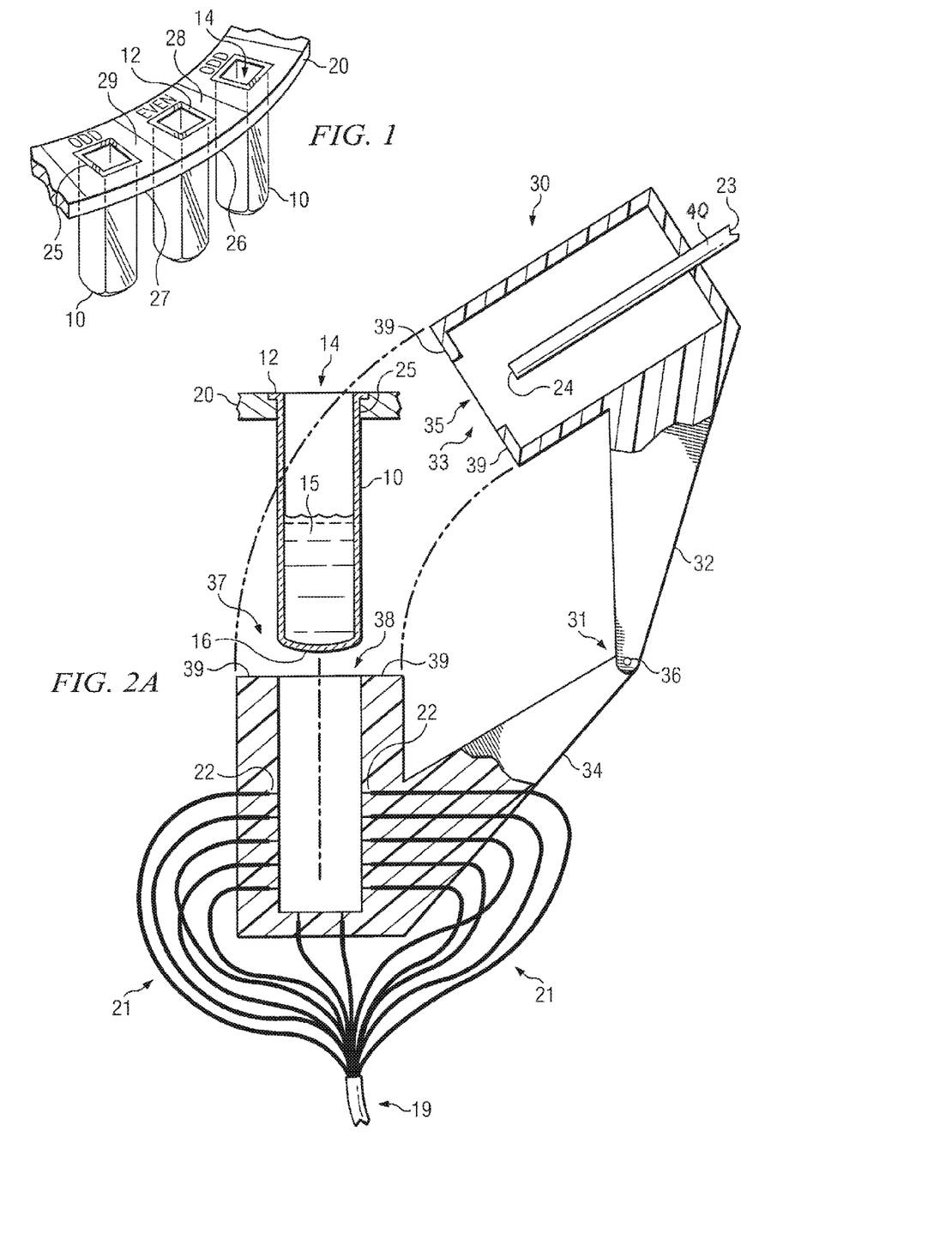
FIG. 1 shows a schematic of reaction cuvettes disposed in a reaction ring.
FIG. 2A shows a schematic of an open clam-shell luminometer in accordance with the present invention.

Referring to FIG. 1, there is shown a schematic of reaction cuvettes 10 disposed in adjacent openings 25 in a carousel or reaction ring 20.

Under current assay testing practice, each sample-containing reaction cuvette 10 is removed from the carousel or reaction ring 20 and transported to a luminometer, where the intensity and wavelengths of light generated by the addition of a light-generating reagent are measured to provide a measure of the chemical constituents in the assay reaction mixture. This process requires a gantry and a gripper, an elevator or some other device to grab the reaction cuvette 10; lift it from the opening 25; and transport it to the luminometer. However, removing and transporting the reaction cuvette 10 are undesirable as they require additional structure to perform the steps and there is a risk of jamming and spillage/cross-contamination. Therefore, it would be desirable to provide an analyzer that, at the assay testing location, includes a luminometer that measures intensity and wavelengths while the reaction cuvette 10 remains on the carousel or reaction ring 20. Such a luminometer, which achieves the functionality of measuring light by closing on the carousel or reaction ring 20 during measurement, is desirable.

Figures 2B, 3:
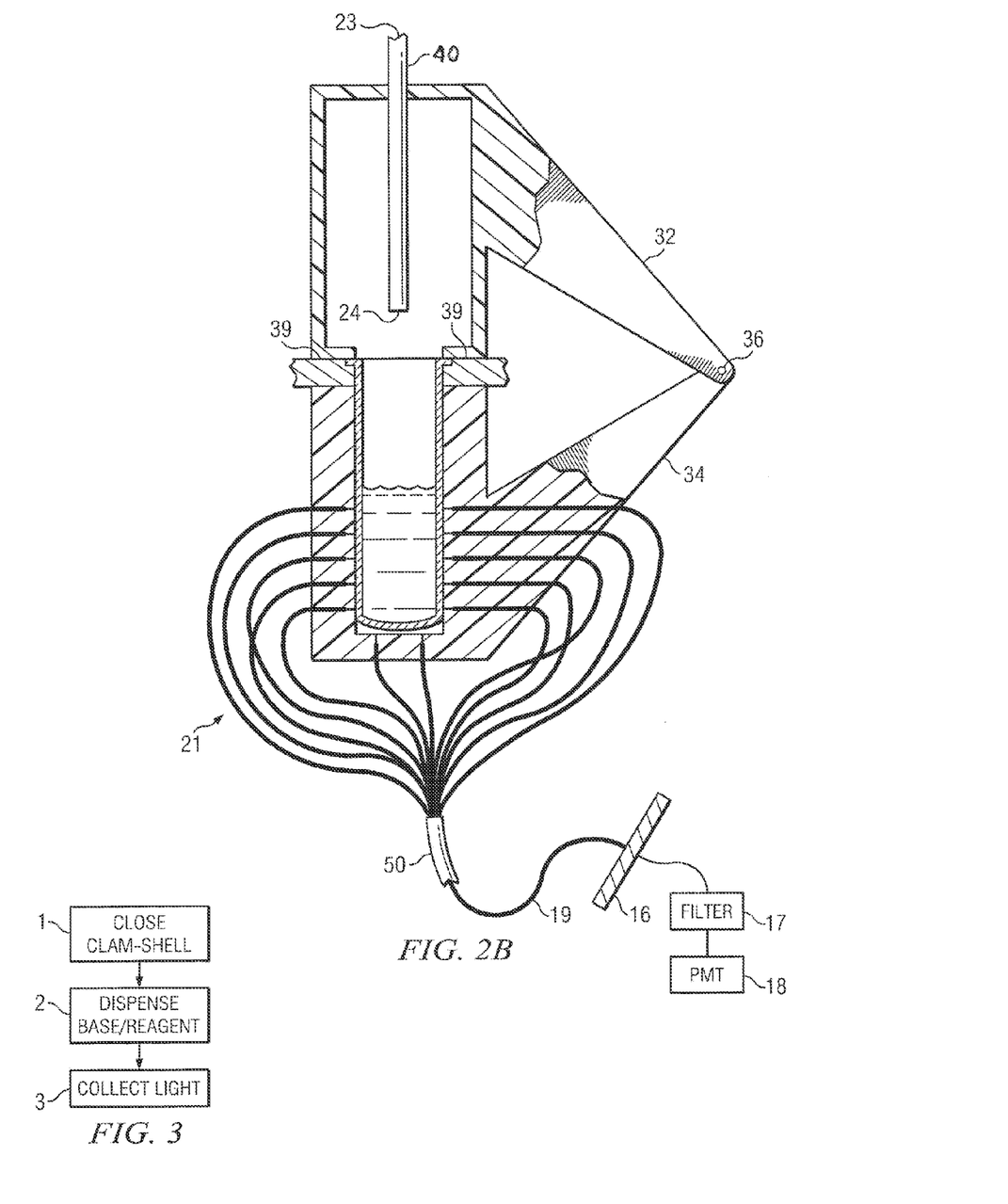
FIG. 2B shows a schematic of the clam-shell luminometer in FIG. 2A when closed in accordance with the present invention.
FIG. 3 shows a flow diagram of a method of performing assay testing using the clam-shell luminometer of FIGS. 2A and 2B.

FIGS. 2A and 2B show, in accordance with an embodiment of the present invention, a clam-shell luminometer 30 in an open and a closed position, respectively. Although the clam-shell luminometer 30 achieves the functionality of measuring light by closing on the carousel or reaction ring 20, instead of by removing reaction cuvettes 10, the invention is not to be construed as being limited thereto. Variations of the clam-shell embodiment are also envisioned and discussed hereinbelow.

Returning to the clam-shell embodiment, in an open position (FIG. 2A), the luminometer 30 is in a dormant state and, in a closed position (FIG. 2B), the luminometer 30 is in an operating state. The luminometer 30 may be disposed in the assay testing area of the analyzer. An analyzer can include a plurality of luminometers 30 however, for this description, an assay testing area having a single luminometer 30 will be described.

The luminometer 30 includes a first or upper portion 32 and a second or lower portion 34 that, at a proximal end 31 of each, are mutually operational and rotationally coupled at a hinge portion 36. It should be noted that the reference to "upper" and "lower" are not limiting but used merely for clarity of explanation of the embodiments of the present invention. Each of the first and second portions 32 and 34 are mechanically coupled to a driving device (not shown), e.g., a motor, that is selectively operable by a controller or processing device (not shown). In one embodiment, the upper and lower portions 32 and 34 are arranged to open and close in like fashion to the jaws of a clam-shell. Alternate hinge mechanisms are envisioned and will be described below.

Each of the upper and lower portions 32 and 34 can be made of a metal, an alloy or a plastic material or a combination thereof that is opaque or that otherwise blocks all ambient light from entering the clam-shell when it is in a closed position. To further block ambient light from entering the clam-shell when it is in a closed position, a compliant, deformable material 39, i.e., a skirt, is integrated into one or both of the upper and lower portions 32, 34 so as to circumscribe the peripheries of the mating surfaces between the upper 32 and lower portions 34.

At the distal end 33 of the first portion 32 is an opening and a first cavity area 35 that is configured to completely cover and enclose the lip 12 and any portion of the reaction cuvette 10 above the carousel or reaction ring 20. Optionally, the distal end 33 of the first portion 32 also includes notched portions (not shown) that are adapted to mate with top portions 28 and 29 of the carousel or reaction ring 20 immediately adjacent to the opening 25 and reaction cuvette 10.

At the distal end 37 of the second portion 34 is an opening and a second cavity area 38 that is configured to completely cover and enclose that portion of the reaction cuvette 10 below the reaction ring 20. Optionally, the distal end 37 of the second portion 34 also includes notched portions (not shown) that are adapted to mate with bottom portions 26 and 27 of the carousel or reaction ring 20 immediately adjacent to the opening 25 and reaction cuvette 10.

Although the embodiment of the luminometer 30 described above uses upper and lower portion 32 and 34 that are brought together by rotating the portions towards the carousel or reaction ring 20 and towards each other in an arc, this is for the purpose of illustration and not limitation. Alternatively, one or both of the upper and lower portions 32 and 34 can be configured to approach the carousel or reaction ring 20 from a vertical or substantially vertical direction, normal or substantially normal to the surface 28, 29 of the carousel or reaction ring 20. This approach may be provided by a vertical screw between the two portions 32, 34 or an offset channel and hinge, by provision of a cam, etc. One of ordinary skill in the art will understand the different types of hinges, or other arrangements, that may be used to accomplish the teachings found herein.

In another embodiment, instead of approaching the reaction cuvette 10 from a top and bottom, the luminometer (not shown) can be configured to approach the reaction cuvette 10 and the carousel or reaction ring 20 from the side, i.e., horizontally.

Still further, one of the upper and lower portions 32, 34 may be brought into position first, with the other portion then positioned.

A light-generating reagent conduit 40 is integrated into the first portion 32, to dispense a desired volume of light-generating reagent into the reaction cuvette 10 once the luminometers is in the closed position. The light-generating reagent conduit 40 is positioned within the first portion 32 so that, when the luminometer 30 is in a closed position, the distal end 24 of the conduit 40 remains a desired distance from the reaction cuvette 10. Alternatively, when in a closed position, the distal end 24 of the conduit 40 extends through the opening 14 and into the reaction cuvette 10. The alternative arrangement would reduce splashing that may occur when dispensing the light-generating reagent into the reaction cuvette 10.

The proximal end 23 of the light-generating reagent conduit 40 is fluidly coupled to a light-generating reagent source (not shown). Those of ordinary skill in the art can appreciated that a fluid pump (not shown) and a controller (not shown) can be used to dispense a desired volume of light-generating reagent into the reaction cuvette 10.

Figure 4:
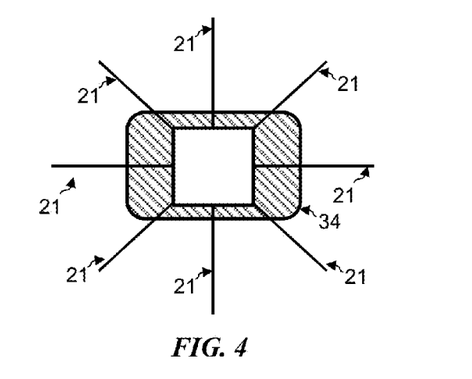
FIG. 4 shows a top-down view of the lower portion of the clam-shell luminometer in accordance with the present invention.

A plurality of fiber optic bundles 21 is or pluralities of fiber optic bundles 21 are integrated into the second portion 34 of the luminometer 30. The fiber optic bundles 21 are adapted to collect and to transport portions of the chemo-luminescent light generated during assay testing, which is to say once light-generating reagent is added to an assay reaction mixture 15 within a reaction cuvette 10 disposed within the second cavity 38. Exposed ends 22 of each of the fiber optic bundles 21 are positioned completely, i.e., 360 degrees (as shown in FIG. 4), around the perimeter or periphery, as well as about the bottom of the second cavity 38 in order to receive light from, i.e., optically coupled with, the second cavity 38. The outer peripheries of the exposed ends 22 of the fiber optic bundles 21 can be fused together in one or more groups. Alternatively or in addition, all of the exposed ends 22 can be retained in or fixedly attached to a ring (not shown) or other device that circumscribes the perimeter/periphery as well as the bottom of the second cavity 38.

Advantageously, each of the fiber optic bundles 21 positioned completely around the perimeter/periphery and the bottom of the second cavity 38 collects some portion of the light generated in the assay reaction mixture 15 from the sides and the bottom 16 of the reaction cuvette 10. This provides a more accurate and more complete measure of chemo-luminescent light emitted during the assay testing than would be the case with conventional luminometers, which, typically, only receive light from about half or less than half of the perimeter/periphery of the reaction cuvette 10.

Optionally, instead of disposing the first, exposed ends 22 of the fiber optic bundles 21 in the second portion 34 in order to be adjacent to the perimeter/periphery and bottom 16 of the reaction vessel 10, an elliptical mirror (not shown) is integrated into the second portion 34. The elliptical mirror reflects light from all around the reaction cuvette 10 to, for example, an edge of the lower portion 34 where the exposed ends 22 of the fiber optic bundles 21 are arranged for that purpose.

Figure 5:
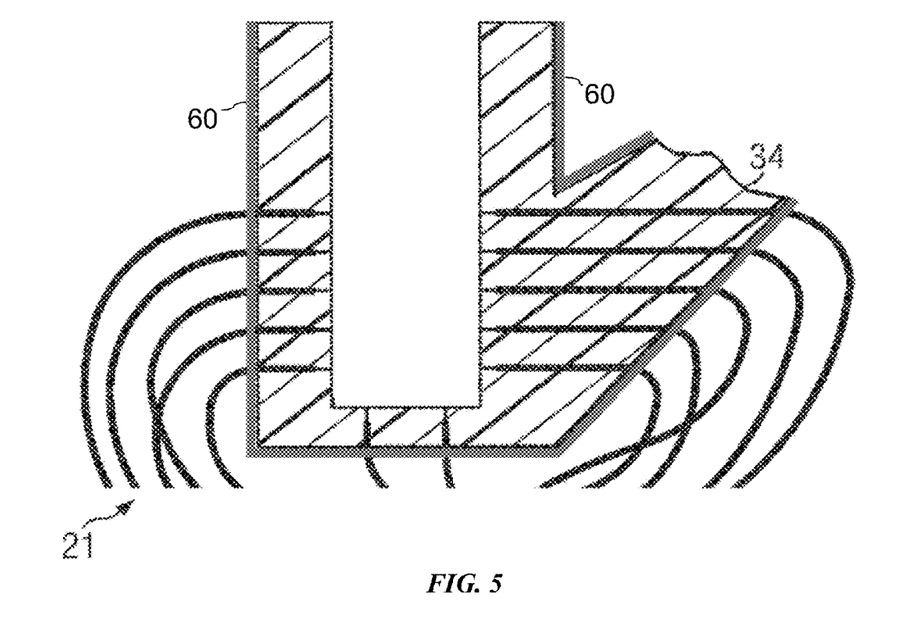
FIG. 5 shows a view of the lower portion of the clam-shell luminometer in accordance with another embodiment of the present invention.

Yet another option, as shown in FIG. 5, is to use a solid transparent body, made of acrylic, glass, or similar transparent material, for the lower portion 34 surrounding the part of the cuvette 10 that emits the light, with its exterior covered with an opaque coating 60 to prevent ambient light interference, that transmits and pipes the light via internal reflections to the end of the fiber optic bundle.

Second ends 19 of the fiber optic bundles 21 are mechanically and optically coupled to at least one light intensity-measuring device 18, e.g., a phototube, a photodiode, a photomultiplier tube (PMT), a CCD/CMOS image sensor, and the like, as shown in FIG. 2B. Although embodiments of the invention will be described using a PMT 18 as a light intensity-measuring device 18, this is for illustrative purposes only and not for the purpose of limitation. Indeed, any light intensity-measuring device that is capable of measuring intensity and wavelengths can be used in its place. The operation and function of the PMT 18 or other light intensity-measuring device 18 are well known to those of ordinary skill in the art and will not be described in any great detail. Suffice it to say that a PMT 18 can operate in an analog mode, whereby it measures current flow as a function of light intensity, or in a photon counting mode, whereby it measures the bursts of current caused by photons striking the tube (not shown) of the PMT 18. Output data signals from the PMT 18 are transmitted to a signal processing electronic circuit (not shown).

To prevent ambient light from affecting and damaging the PMT 18 when the luminometer 30 is in an opened position, a shutter 16 can be optically coupled between the second ends 19 of the fiber optic bundles 21 and the PMT 18. Consequently, when the luminometer 30 is in an opened position, the shutter 16 is closed, blocking light from damaging the PMT 18, and when the luminometer 30 is in a closed position, the shutter 16 is open, allowing the free flow of collected light.

Although, FIGS. 2A and 2B depict individual second ends 19 randomly oriented, this is done for the purpose of illustration and not for the purpose of limitation. Ideally, the peripheries of the second ends 19 of the fiber optic bundles 21 can be fused together in a single or multiple groups. Alternatively or in addition, the running portion and second ends 19 of the fiber optic bundles 21 can be enclosed in a conduit(s) 50. Such a conduit, in one embodiment, is made from an opaque material to block ambient light from affecting measurements.

Figure 6:
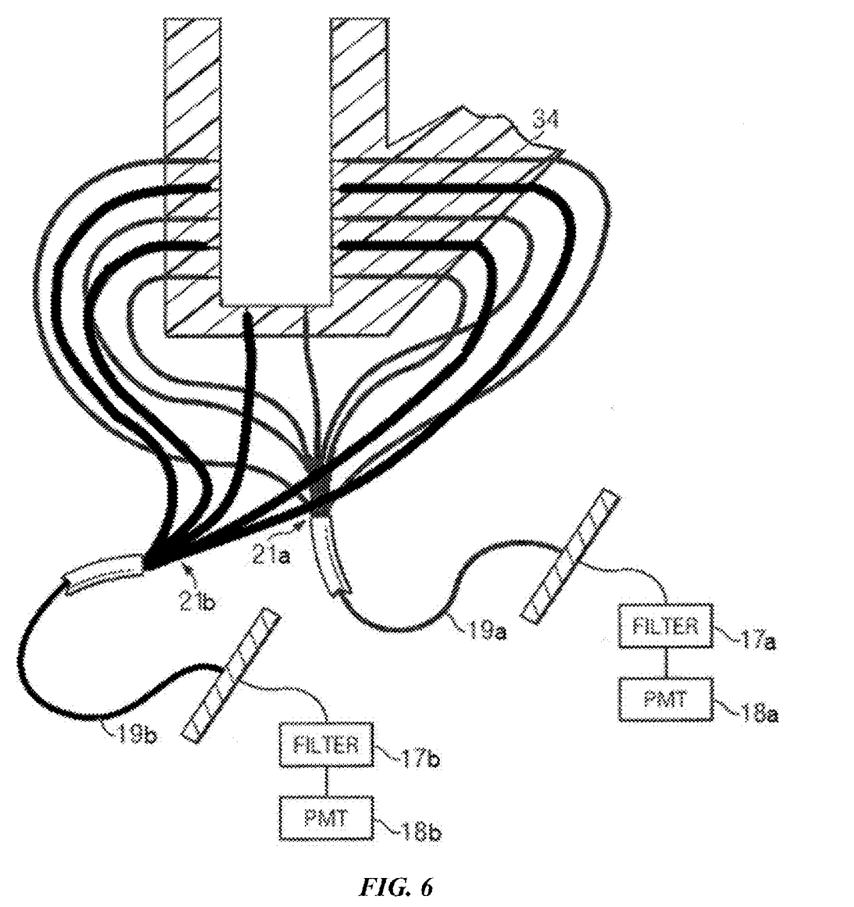
FIG. 6 shows a view of the lower portion of the clam-shell luminometer in accordance with a further embodiment of the present invention.

Advantageously, fiber optic bundles 21 surrounding the perimeter/periphery and bottom of the second cavity 38 can be used for assay multiplexing, by which two or more assays are carried out on the same sample in the same reaction cuvette 10 at the same time. For example, as shown in FIG. 6 the second ends 19a of a first group of fiber optic bundles 21a can be optically coupled to a first PMT 18a, while the second ends 19b of a second group of fiber optic bundles 21b are optically coupled to a second PMT 18b. Each of the PMTs 18a, 18b would include a corresponding optical filter 17a, 17b that is disposed between the second ends 19a, 19b and the PMTs 18a, 18b. Each of the optical filters 17a, 17b, e.g., notch filters, is adapted to pass collected light at discrete wavelengths or wavelength bands. Each assay, in turn, would be engineered to emit light at different wavelengths for each chemical compound being measured.

Having described a luminometer and an improved immunoassay analyzer having the same, a method of testing assay reaction mixtures automatically using the luminometer will now be described. Advantageously, the method of the present invention does not require removing reaction cuvettes from the carousel or reaction ring, but, rather, in bringing the luminometer to the reaction cuvette.

FIG. 3 provides a flow diagram of one embodiment of an assay-testing method in accordance with an embodiment of the present invention. For the purpose of this discussion, it is assumed that the assay reaction mixture has been aspirated from a sample-containing vessel and dispensed into a reaction cuvette, reagents have been added, and, if required, one or more washing operations has been completed and the assay reaction mixture has been resuspended. In short, it is assumed that the assay reaction mixture is ready for assay testing and that the reaction cuvette containing the assay reaction mixture is located at the signal measurement position of the automated analyzer.

In a first step, the controller causes the motor to move the first and second portions 32, 34 of the luminometer 30 from the open position to the closed position (STEP 1). As previously described, the opening in the first portion 32 encloses the lip of the reaction cuvette 10 and any portion of the reaction cuvette 10 that is disposed above the carousel or reaction ring 20 and the optional notched portion mates with the carousel or reaction ring 20. In the closed position, the first and second portions 32, 34 cover and enclose the reaction cuvette 10 and keep out any ambient and/or transient light that is not generated by the reaction of the light-generating reagent and the assay reaction mixture 15. Similarly, the opening and optional notched portion in the second portion 34, respectively, enclose that portion of the reaction cuvette 10 that is disposed below the carousel or reaction ring 20 and mate with the carousel or reaction ring 20, also to cover and enclose the reaction vessel and to block out any ambient and/or transient light.

Having enclosed the reaction cuvette 10 and isolated it from external light sources, the controller causes a pump to dispense a desired volume of light-generating reagent (STEP 2) from the light-generating reagent source into the reaction cuvette 10. Once the light-generating reagent mixes with the assay reaction mixture, chemo-luminescent light indicative of the quantity and chemical constituents of the assay reaction mixture is generated and the generated light is collected (STEP 3) through the exposed ends of the plurality of fiber optic bundles 21. Advantageously, because the exposed ends of the fiber optic bundles are arranged with respected to the second cavity 38 to completely surround the perimeter/periphery and bottom of the reaction cuvette 10, a more complete and more accurate measure of the intensity and wavelengths of the collected light can be made and made with relatively high gain and relatively low noise.

The collected light travels through the fiber optic bundles 21 to the PMT 18, which processes the collected light and measures the intensity and wavelengths. Prior to reaching the PMT 18 the collected light may be filtered. Filtering is especially important during assay multiplexing when two or more assays are performed on the same sample assay in the same reaction cuvette 10 at the same time.

As is well known to the pertinent art, PMTs 18 can operate in an analog mode, in which current flow as a function of the light intensity is measured, or in a photon-counting mode, in which bursts of current caused by photons hitting the tube of the PMT 18 are measured. Regardless of the mode of operation, these PMT-measured data are provided to signal processing electronic circuitry, which further processes the data to provide a desired output in a desired format.

A luminometer, an improvement for an automated analyzer that includes the luminometer, and a method of performing assay testing using both described above assume that light measurement follows dispensing a light-generating reagent into the sample assay. However, embodiments of the present invention include other methods of light measurement many of which do not require the addition of a light-generating reagent into the sample assay, relying, instead, on shining a light, e.g., a collimated beam, a laser, and the like, on the sample assay and collecting the reflected or refracted light.

Figure 7:
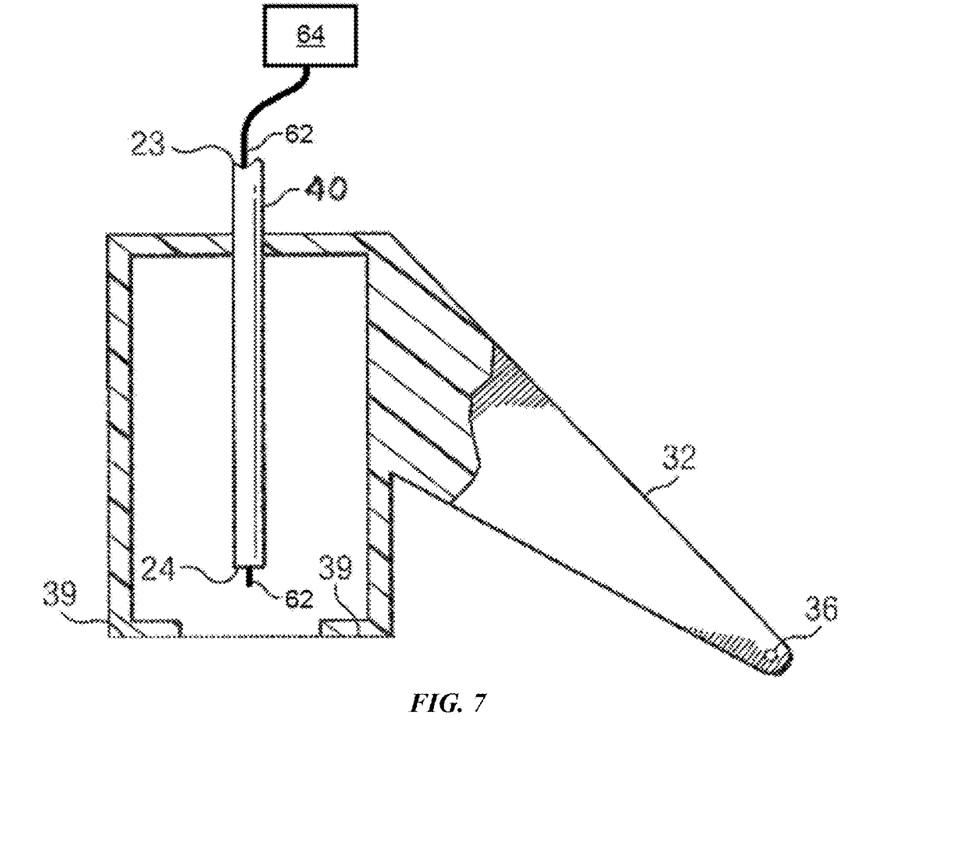
FIG. 7 shows a view of the upper portion of the clam-shell luminometer in accordance with another embodiment of the present invention.

For example, one such technique involves generating light in a sample assay using fluorescence. For example, the clam-shell luminometer 30 described hereinabove can be modified as shown in FIG. 7 so that a separate plurality of transmitting fiber optic bundles 62 optically coupled to a light-generating or light-emitting source 64 are routed through the light-generating reagent conduit 40 so that the exposed ends of the separate fiber optic bundles 62 are disposed at a desired distance from the reaction cuvette 10 and/or from the assay reaction mixture 15. The light source 64 emits light, e.g., a laser, a collimated light, and so forth, at an appropriate excitation wavelength for the discrete assay reaction mixture. Light generated in the assay reaction mixture through fluorescence is collected by at least one of the plurality of fiber optic bundles 21.

There may be multiple groups of fiber optic bundles 21 and a group of one or more fiber optic bundles 21 may be optically coupled to a corresponding filter 17, to provide light intensity data for a variety of wavelengths. Moreover, the exposed ends 22 of all of these groups of fiber optic bundles 21 may be arranged to be perpendicular or substantially perpendicular to the direction of the incident light from the light source.

Nephelometry is also possible using the teachings of the present invention. Nephelometry differs from the fluorescence embodiment described hereinabove in that light scattered by the assay reaction mixture is collected at an angle from the direction of the incident light. In this instance, the angle does not have to be orthogonal or substantially orthogonal to the direction of the incident light as with fluorescence.

Luminescent oxygen channeling immunoassay (LOCI) techniques are also feasible with embodiments of the present invention. Here again, light shining on the assay reaction mixture 15 generates light at different wavelengths through singlet oxygen channeling. Light generated in the assay reaction mixture 15 through LOCI is subsequently collected by the plurality of fiber optic bundles 21.

Although various embodiments of the present invention have been described above, it will be recognized and understood that various modifications may be made and that the appended claims are intended to cover all such modifications which fall within the spirit and scope of the invention.

What I claim is:

1. A luminometer for use with a reaction vessel having an open top end and a bottom end, the luminometer comprising:
    a carousel having an opening configured to hold the reaction vessel;
    a first portion having a first cavity with a first cavity opening sized to mate with a top side of the carousel;
    a second portion having a second cavity with a second cavity opening sized to mate with a bottom side of the carousel and to enclose the bottom end of the reaction vessel when disposed in the opening in the carousel;
    a plurality of fiber optic bundles, each having a first end, a second end, and a running length therebetween, the first ends of each of the fiber optic bundles optically coupled to the second cavity and disposed around a perimeter and a bottom of the second cavity; and
    a conduit disposed in the first portion, such that, when the luminometer is in the closed configuration, a distal end of the conduit will be positioned a predetermined distance from a reaction vessel disposed in the second portion,
    wherein each of the first and second portions are configured to block ambient light from the first and second cavities, respectively, when the luminometer is in a closed configuration, and
    wherein the conduit is configured to receive a transmitting fiber optic bundle which provides light at an excitation wavelength.

2. The luminometer as recited in claim 1, wherein the first ends of the plurality of fiber optic bundles are arranged to provide 360° coverage in a lateral plane about the second cavity.

3. The luminometer as recited in claim 1, wherein each of the first and second portions comprises a material that prevents the transmission of light.

4. The luminometer as recited in claim 1, wherein the second portion comprises a solid transparent body, and
    wherein an exterior surface of the solid transparent body is covered with an opaque coating to prevent ambient light interference.

5. The luminometer as recited in claim 4, wherein the solid transparent body is formed of a material selected from the group consisting of acrylic and glass.

6. The luminometer as recited in claim 1, further comprising:
    at least one light-intensity measuring device coupled to the second ends of the plurality of fiber optic bundles.

7. The luminometer as recited in claim 6, wherein the at least one light-intensity measuring device is selected from the group consisting of a photomultiplier tube, a CCD/CMOS image sensor, a photodiode and a phototube.

8. The luminometer as recited in claim 6, wherein the at least one light-intensity measuring device includes a shutter that is configured to block the transmission of light to said at least one light-intensity measuring device when the luminometer is in an open configuration.

9. The luminometer as recited in claim 6, further comprising:
    first and second light-intensity measuring devices,
    wherein the first measuring device is optically coupled to a first discrete group of the plurality of fiber optic bundles, and
    wherein the second measuring device is optically coupled to a second discrete group of the plurality of fiber optic bundles.

10. The luminometer as recited in claim 9, wherein each of the first and second light-intensity measuring devices includes an optical filter that is adapted to filter light transmitted through the respective discrete group of fiber optic bundles at a predetermined wavelength or range of wavelengths.

11. The luminometer as recited in claim 1, wherein the conduit is configured to convey a liquid reagent.

12. The luminometer as recited in claim 1, wherein the transmitting fiber optic bundle is configured to be positioned a desired distance from a reaction vessel disposed in the second portion when in the closed configuration.

13. The luminometer as recited in claim 12, wherein a group of the plurality of fiber optic bundles are adapted to collect emitted light at a different wavelength than an excitation wavelength and in a direction substantially perpendicular to light emitted from the transmitting fiber optic bundle.

14. The luminometer as recited in claim 12, wherein a group of the plurality of fiber optic bundles are adapted to collect emitted light at an angle with respect to a direction of the light emitted from the transmitting fiber optic bundle.

15. A luminometer for use with an immunoassay analyzer, the luminometer configured to enclose a reaction vessel, the reaction vessel having a lip at an open end and a bottom at a closed end and being disposed in an opening in a carousel, the luminometer comprising:
 first and second portions that are adapted to mate with, respectively, a top side and a bottom side of the carousel:
  the first portion having an opening that is configured to enclose the lip of the reaction vessel disposed in the carousel when the luminometer is in a closed configuration, and
  the second portion having an opening that is configured to enclose that portion of the reaction vessel that is below the reaction carousel;
 at least one light-intensity measuring device; and
 a plurality of fiber optic bundles, each having a first end, a second end, and a running length therebetween, the first ends of each of the fiber optic bundles being disposed in the second portion and the second ends of each of the fiber optic bundles being optically coupled to the at least one light intensity-measuring device,
 wherein the first ends of the plurality of fiber optic bundles surround the perimeter and the bottom of the second portion, and
 wherein the first and second portions are hingeably coupled to each other.

16. The luminometer as recited in claim 15, wherein the first ends of the plurality of fiber optic bundles provide a 360 degree coverage in a lateral plane about the reaction vessel.

17. The luminometer as recited in claim 15, wherein each of the first and second portions of the luminometer are made of a material that prevents the transmission of light.

18. The luminometer as recited in claim 15, wherein each of the first and second portions of the luminometer includes a mating portion comprising a compliant material.

19. The luminometer as recited in claim 15, wherein the at least one light-intensity measuring device is selected from the group consisting of a photomultiplier tube, a CCD/CMOS image sensor, a photodiode and a phototube.

20. The luminometer as recited in claim 15, wherein each of the at least one light-intensity measuring device includes a shutter that is capable of blocking light to said at least one light-intensity measuring device when the luminometer is in the open configuration.

21. The luminometer as recited in claim 15, wherein the second portion comprises a solid transparent body, and wherein an exterior surface of the solid transparent body is covered with an opaque coating to prevent ambient light interference.

22. The luminometer as recited in claim 21, wherein the transparent body is made from a material selected from the group consisting of acrylic and glass.

23. The luminometer as recited in claim 15, wherein there are multiple light-intensity measuring devices, each of which is optically coupled to a respective discrete group of the plurality of fiber optic bundles.

24. The luminometer as recited in claim 23, wherein each of the multiple light-intensity measuring devices includes an optical filter that is adapted to filter collected light transmitted through the respective discrete group of fiber optic bundles at a predetermined wavelength.

25. The luminometer as recited in claim 15, further comprising:
 a conduit disposed in the first portion, such that, when the luminometer is in the closed configuration, a distal end of the conduit is positioned a desired distance from a reaction vessel disposed in the second portion.

26. The luminometer as recited in claim 25, wherein the conduit is configured to convey a liquid reagent.

27. The luminometer as recited in claim 26, wherein a group of the plurality of fiber optic bundles and the at least one light-intensity measuring device are adapted to collect emitted light resulting from fluorescence at a different wavelength than an excitation wavelength and in a direction perpendicular or substantially perpendicular to light emitted from the transmitting fiber optic bundle.

28. The luminometer as recited in claim 25, wherein the conduit is configured to receive a transmitting fiber optic bundle which provides light at an excitation wavelength.

29. The luminometer as recited in claim 28, wherein the conduit is configured to receive a transmitting fiber optic bundle to be positioned a desired distance from a reaction vessel disposed in the second portion when in the closed configuration.

30. The luminometer as recited in claim 29, wherein a group of the plurality of fiber optic bundles and the at least one light intensity-measuring device are adapted to collect emitted light at an angle to a direction of the light emitted from the transmitting fiber optic bundle.

31. The luminometer as recited in claim 29, wherein light emitted from the transmitting fiber optic bundle is adapted to generate light at different wavelengths in an assay reaction mixture.

32. The luminometer as recited in claim 15, wherein the second portion comprises a compliant, deformable material configured to circumscribe the periphery of the mating surface of the second portion and the bottom side of the carousel.

* * * * *